(12) United States Patent
Horiguchi et al.

(10) Patent No.: US 7,276,382 B2
(45) Date of Patent: Oct. 2, 2007

(54) BLOOD TESTING METHOD

(75) Inventors: Noboru Horiguchi, 2969-1, Kawatsu-cho, Sakaide-shi, Kagawa-ken (JP); Hiroshi Horiguchi, Sakaide (JP)

(73) Assignee: Noboru Horiguchi (JP)

( * ) Notice: Subject to any disclaimer, the term of this patent is extended or adjusted under 35 U.S.C. 154(b) by 748 days.

(21) Appl. No.: 10/676,107

(22) Filed: Oct. 2, 2003

(65) Prior Publication Data

US 2005/0074893 A1    Apr. 7, 2005

(51) Int. Cl.
*G01N 1/18* (2006.01)
*G01N 33/48* (2006.01)

(52) U.S. Cl. ............... 436/177; 436/63; 436/174; 436/175; 436/45; 435/2

(58) Field of Classification Search ............ 436/14, 436/63, 70, 174, 175, 177, 45; 435/2
See application file for complete search history.

(56) References Cited

U.S. PATENT DOCUMENTS

| 4,142,857 A | 3/1979 | Acuff .................... 23/230 |
| 7,090,862 B2 * | 8/2006 | Barrett-Reis et al. ....... 424/439 |
| 2002/0025546 A1 | 2/2002 | Komori et al. ............... 435/28 |

FOREIGN PATENT DOCUMENTS

| GB | 996089 | * | 6/1965 |
| SU | 1 115 723 A | | 9/1984 |

OTHER PUBLICATIONS

Patent Abstracts of Japan, vol. 13, No. 40 (P-820), Jan. 30, 1989.
Lester, E., "The Clinical Value of Glycated Hemoglobin and Glycated Plasma Proteins", Annals of Clinical Biochemistry, vol. 26, No. 3, 1989, pp. 213-219.

* cited by examiner

*Primary Examiner*—Maureen M. Wallenhorst
(74) *Attorney, Agent, or Firm*—Bacon & Thomas, PLLC

(57) ABSTRACT

A blood test method including (a) centrifuging a mammalian blood sample into a plasma and blood cells; (b) removing buffy coats from the blood cells to obtain red blood cells containing solutes confined therewithin; (c) washing the red blood cells with a buffered physiological saline solution and isolating the washed blood cells; (d) mixing the washed red blood cells with a buffered physiological saline solution to obtain a suspended liquid; (e) centrifuging the suspended liquid to remove a supernatant and to obtain a red blood layer; (f) mixing the red blood layer with a hypertonic solution and maintaining the resulting suspension at a temperature of 25 to 40° C. for a period of time sufficient for the solutes confined in the red blood cells to penetrate into the hypertonic solution; (g) centrifuging the suspension to obtain a supernatant containing the solutes; and (h) measuring the supernatant for at least one factor selected from a glucose concentration, a pyruvic acid concentration, a lactic acid concentration and an oxidation-reduction potential.

16 Claims, 1 Drawing Sheet

BLOOD TESTING METHOD

BACKGROUND OF THE INVENTION

1. Field of the Invention

This invention relates to a blood testing method for early detection of diseases.

2. Description of Prior Art

Biochemical analysis of a body fluid such as blood is currently increasingly conducted for diagnosing various sicknesses in many hospitals. In the case of diagnosis of diabetes, for example, blood samples before and after meal are generally analyzed for the concentration of glucose therein.

Glucose is a source of energy for human body's cells and is released from the liver into blood. In a healthy individual, the release of glucose from the liver and the utilization of glucose in the cells are balanced so that the blood glucose level is maintained at about 110 mg/dL or less. Insulin is a hormone secreted from pancreas and necessary for the human body to properly convert sugar, starches and other food into a cellular energy source. When starch is digested in the small intestine, the level of glucose present in the blood increases. Such an increase in the blood glucose level stimulates increased secretion of insulin so that the liver stops releasing the glucose. Upon intracellular utilization of the glucose, the blood glucose decreases to the normal level. Such increase and decrease of the blood glucose level are repeated every time a healthy individual takes foods.

Some individuals are unable to quickly or sufficiently secrete insulin even when their blood glucose level rises after meal. When insufficient exercise and excess ingestion are added to this condition, glucose remains excessively in blood so that the blood glucose level does not decrease even after several hours from the intake of meals.

In the conventional biochemical analysis, the blood glucose level is measured by isolating plasma from blood samples taken before and after meals. When the glucose concentration in a plasma sample obtained in an empty stomach stage is greater than 140 mg/dL or when the glucose concentration in a plasma sample taken just after meal is greater than 200 mg/dL, then he or she is diagnosed as being diabetic (type-2 diabetes). A high glucose level when continued for a long time will cause heart, circulation, eye and kidney problems.

There are recent reports concerning symptoms of cardiac infarction in individuals whose blood glucose levels were found to be not significantly high when measured with the conventional plasma test method. Namely, it has been found that arteriosclerosis proceeds even in prediabetics. Especially, individuals whose insulin secretion is slow are likely to cause arteriosclerosis when they meet with one or more conditions of mild type-2 diabetes, slight overweight, mild hyperlipidemia and light hyperinsulinemia. The conventional blood test methods in which plasma of a blood sample is measured for the concentration of glucose is not effective for the early detection of diabetes. Thus, there is an urgent demand for a diagnostic method capable of precisely detecting diabetes and other diseases even at their early stages.

BRIEF SUMMARY OF THE INVENTION

With the conventional blood test methods in which plasma of a blood sample is measured for components such as glucose and lactic acid, the measured values merely represent those of the components exuded and released from the blood cells into the plasma. It has been found that in order to detect diabetes and other diseases at their early stages it is important that components contained in red blood cells should be measured. Namely, since red blood cells have metabolic functions to decompose glucose and to precedently control the glucose concentration in the plasma, it is effective to know the glucose level in the red blood cells for the early detection of diabetes. Further, the oxidation-reduction potential in the blood cells and the concentrations of pyruvic and lactic acid which are metabolites of glucose have been found to be important parameters for early detection of various diseases.

It is an object of the present invention to provide a blood test method capable of detecting changes of glucose, pyruvic acid and lactic acid concentrations and oxidation-reduction potential which changes have not yet significantly occurred in plasma.

Another object of the present invention is to provide a blood test method which can precisely diagnose various diseases such as diabetes, cardiac insufficiency, renal insufficiency and chronic respiratory disease, at early stages thereof.

In accordance with the present invention, there is provided a blood test method comprising the steps of:

(a) centrifuging a mammalian blood sample into a plasma and blood cells;

(b) removing buffy coats from said blood cells to obtain red blood cells containing solutes confined therewithin;

(c) washing said red blood cells with a buffered physiological saline solution and isolating said washed blood cells;

(d) mixing said washed red blood cells with a buffered physiological saline solution to obtain a suspended liquid;

(e) centrifuging said suspended liquid to remove a supernatant and to obtain a red blood layer;

(f) mixing said red blood layer with a hypertonic solution and maintaining the resulting suspension at a temperature of 25 to 40° C. for a period of time sufficient for the solutes confined in the red blood cells to penetrate into the hypertonic solution;

(g) centrifuging the suspension to obtain a supernatant containing the solutes; and (h) measuring the supernatant for at least one factor selected from a glucose concentration, a pyruvic acid concentration, a lactic acid concentration and an oxidation-reduction potential.

BRIEF DESCRIPTION OF THE DRAWING

Other objects, features and advantages of the present invention will become apparent from the detailed description of the preferred embodiments of the invention which follows, when considered in light of the accompanying drawing, in which.

DETAILED DESCRIPTION OF THE PREFERRED EMBODIMENTS OF THE INVENTION

Figure 1:
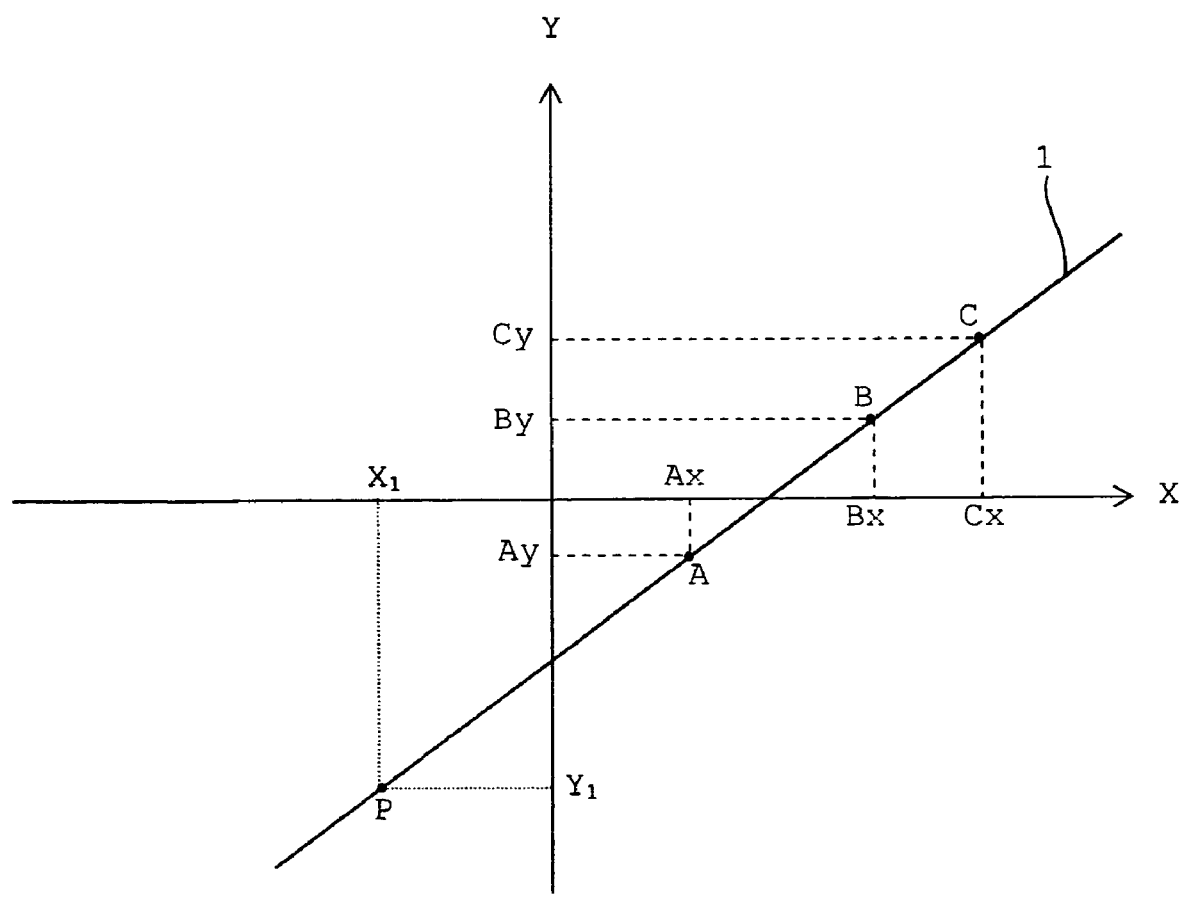
FIG. 1 is an example of a working curve for determining an oxidation-reduction potential.

A blood test method according to the present invention comprises the following steps (a)-(h).

Step (a):

A mammalian blood is sampled and centrifuged into a plasma and blood cells. A conventional intravenous blood sampling tube containing a suitable amount of an anticoagulation agent such as heparin or EDTA may be used for sampling. The blood sample (in an amount of 2 ml, for example) is preferably centrifuged at a force of 130×g to 200×g for 5 to 10 minutes into a plasma and blood cells including red blood cells, white blood cells and platelets.

Step (b):

The blood cells from Step (a) are separated into buffy coats including white blood cells and platelets and red blood cells containing solutes confined therewithin. Preferably, the blood cells from Step (a) are mixed with a sedimentation agent such as metrizamide, and the mixture is centrifuged at a force of 800×g to 1,200×g for 7 to 12 minutes to separate red blood cells from the buffy coats.

Step (c):

The red blood cells obtained in Step (b) are washed with a buffered physiological saline solution and the washed blood cells are isolated. Preferably, the red blood cells are mixed with a phosphate buffered physiological saline solution, and the resulting mixture is centrifuged at a force of 130×g to 200×g for 5 to 10 minutes. As a result of the washing, impurities such as white blood cells, platelets and plasma which deposit on the red blood cells are removed.

Step (d):

The washed red blood cells are mixed with a buffered physiological saline solution to obtain a suspended liquid. Preferably, the washed red blood cells are mixed with a phosphate buffered physiological saline solution in an amount so that the suspended liquid has a hematcrit value of 40 to 50%. More preferably, the phosphate buffered physiological saline solution is added so that 2 ml of the suspended liquid has a hematcrit value of 50%. Alternatively, the washed red blood cells may be mixed with a phosphate buffered physiological saline solution so that the suspended liquid has a number of red blood cells in the range of 4,000,000/μL ($4 \times 10^6$ microliter) to 5,000,000/μL ($5 \times 10^6$ microliter). A customarily employed automatic blood cell counter is suitably used to count the red blood cell number.

Step (e):

The suspended liquid obtained in step (d) is centrifuged to remove a supernatant and to obtain a red blood layer. Preferably, the suspended liquid is centrifuged at a force of 130×g to 200×g for 5 to 10 minutes.

Step (f):

The red blood layer is then mixed with a hypertonic solution and the resulting suspension is maintained at a temperature of 25 to 40° C. for a period of time sufficient for the solutes confined in the red blood cells to penetrate into the hypertonic solution. Preferably, the red blood layer is mixed with a 5 to 10% by weight saline solution in a predetermined amount and the resulting mixture is maintained at a temperature of 35 to 38° C. for 7 to 15 minutes. Because of osmotic pressure, the solution in the blood cells containing glucose, lactic acid, pyruvic acid and other solutes passes through the cell wall and diffuses into the hypertonic solution. In order to efficiently and completely recover the intracellular components while preventing denaturation thereof, it is necessary that the suspension be maintained at 25-40° C.

Step (g):

The suspension obtained in step (f) is centrifuged to obtain a supernatant containing the intracellular components transferred from the red blood cells. Preferably, the suspension is centrifuged at a force of 1,500×g to 2,000×g for 7 to 12 minutes.

Step (h):

The supernatant obtained in Step (g) is measured for at least one factor selected from a glucose concentration, a pyruvic acid concentration, a lactic acid concentration and an oxidation-reduction potential.

The glucose concentration, pyruvic acid concentration and lactic acid concentration may be performed using any customarily suitably employed automatic biochemical analyzer. When 2 ml of a suspended liquid having a hematcrit of 50% is prepared in Step (d), the glucose concentration (mg/dL), lactic acid concentration (mg/dL) and pyruvic acid concentration (mg/dL) are the values obtained by multiplying 2 by the measured values. When a suspended liquid having a specific number of red blood cells is prepared in Step (d), the glucose concentration (mg/dL), lactic acid concentration (mg/dL) and pyruvic acid concentration (mg/dL) may be easily calculated from the measured value, mean red blood cell volume, red blood cell number and the volume of the suspended liquid.

An oxidation-reduction potentiometer is suitably used for measuring the oxidation-reduction potential of the red blood cells (ORP-RBC). In this case, ORP-RBC is determined using a working curve prepared by measuring the oxidation-reduction potential of the serum (ORP-srm) obtained from the same blood sample. When 2 ml of a suspended liquid having a hematcrit of 50% is prepared using a 5% by weight saline solution in Step (d), the working curve is typically prepared by the method described below.

From 4 ml of the venous blood sample, a serum is separated by centrifuging the sample at 3,000 rpm for 10 minutes. The oxidation-reduction potential of the serum (Ax) is measured with a potentiometer. The serum is diluted with the same volume of a 5% by weight saline solution and the oxidation-reduction potential of the diluted serum (Ay) is measured. Separately, the serum is diluted with the same volume of a phosphate buffered saline solution (PBS) and the oxidation-reduction potential of the diluted serum (Bx) is measured. The PBS-diluted serum is further diluted with the same amount of a 5% by weight saline solution and the oxidation-reduction potential of the diluted serum (By) is measured. Additionally, the original serum is diluted with three times the volume of PBS and the oxidation-reduction potential of the diluted serum (Cx) is measured. The PBS-diluted serum is further diluted with the same amount of a 5% by weight saline solution and the oxidation-reduction potential of the diluted serum (Cy) is measured. As shown in FIG. 1, the values Ax, Bx and Cx in the X-axis are plotted against the values Ay, By and Cy in the Y-axis, respectively. A curve 1 passing the point A (Ax, Ay), point B (Bx, By) and the point C (Cx, Cy) represents the working curve. The coordinates of the points A (Ax, Ay), B (Bx, By) and C(Cx, Cy) are summarized in Table 1 below.

TABLE 1

| | Point | | |
|---|---|---|---|
| Axis | A | B | C |
| X | Ax: ORP of original serum (non-diluted) | Bx: ORP of 2-fold dilution of original serum with PBS | Cx: ORP of 4-fold dilution of original serum with PBS |
| Y | Ay: ORP of 2-fold dilution of above serum with 5% | By: ORP of 2-fold dilution of above serum with 5% saline | Cy: ORP of 2-fold dilution of above serum with 5% saline |

TABLE 1-continued

| | Point | | |
|---|---|---|---|
| Axis | A | B | C |
| | saline solution | solution | solution |

A point P in the working curve having the Y-axis value Y1 which equals the oxidation-reduction potential of the red blood cells as measured in Step (h) is then determined. The value of the X-axis (X1) of the point P represents the oxidation-reduction potential of the red blood cells (ORP-RBC).

Incidentally, the oxidation-reduction potential using a potentiometer, a potential of the reference electrode must be added to the measured value. The reference electrode potential varies with the temperature of the supernatant. Temperature dependency of the potential of the reference electrode PTS-2019C is as shown in Table 2.

TABLE 2

| Temperature (° C.) | Potential (mV) |
|---|---|
| 0 | 224 |
| 5 | 221 |
| 10 | 217 |
| 15 | 214 |
| 20 | 210 |
| 25 | 206 |
| 30 | 203 |
| 35 | 199 |
| 40 | 196 |
| 45 | 192 |
| 50 | 188 |
| 55 | 185 |
| 60 | 181 |

The following examples will further illustrate the present invention.

EXAMPLE 1

37 patients with type-2 Non-Insulin Dependent Diabetes Mellitus (NIDDM) and 52 healthy persons were each tested for D-glucose concentration in red blood cells according to the following method.

Venous blood (2 ml) was sampled (hepalin was used as an anticoagulation agent) and centrifuged at a force of 150×g for 5 minutes into a plasma and blood cells. The blood cells were mixed with 0.2 ml of metrizamide, and the mixture was centrifuged at a force of 1,000×g for 10 minutes to separate red blood cells from the buffy coats. The red blood cells were washed with a phosphate buffered physiological saline solution, and the resulting mixture was centrifuged at a force of 150×g for 5 minutes. The washed red blood cells were mixed with a phosphate buffered physiological saline solution in an amount so that 2 ml of a suspended liquid having a hematcrit value of 50% was obtained. An automatic blood cell counter was employed to control the hematcrit. The suspended liquid obtained was centrifuged at a force of 150×g for 5 minutes to obtain a red blood layer. The red blood layer was then mixed with a 5% by weight saline solution and the resulting mixture (2 ml) was maintained at a temperature of 37° C. for 10 minutes to obtain a suspension. The suspension was centrifuged at a force of 1,750×g for 10 minutes to obtain a supernatant containing the intracellular components transferred from the red blood cells. The supernatant was measured for its glucose concentration using a biochemical analyzer.

A blood glucose level in plasma was also measured in the conventional method.

In the case of the NIDDM patients, it was found that the higher the blood glucose level in the plasma, the higher was the glucose concentration in the red blood cells. The patient having 350 mg/dL of a blood glucose level in the plasma had 50 mg/dL of a glucose concentration in the red blood cells. In the case of the healthy individuals, too, it was found that the higher the blood glucose level in the plasma, the higher was the glucose concentration in the red blood cells. The individual having 150 mg/dL of a blood glucose level in the plasma had 10 mg/dL of a glucose concentration in the red blood cells. From the above results, it is evident that there is a correlation between the blood glucose level in the plasma and the glucose concentration in the red blood cells.

EXAMPLE 2

A blood cell test according to the present invention was carried out for a diabetes mellitus patient (male, 70 years old) to determine oxidation-reduction potential (ORP), lactic acid concentration, pyruvic acid concentration and pH in the red blood cells in the same manner as described in Example 2. Also measured were oxidation-reduction potential (ORP), lactic acid concentration, pyruvic acid concentration and pH in the plasma in the conventional manner. CPK, myoglobin, LDH and aldolase values were also measured in the conventional manner. The results are summarized in Table 3.

TABLE 3

| | Measurement 1 | Measurement 2 |
|---|---|---|
| In red blood cell | | |
| ORP | 248 mV | 221 mV |
| Lactic acid | 10.6 mg/dL | 18.4 mg/dL |
| Pyruvic acid | 0.68 mg/dL | 1.2 mg/dL |
| pH | 7.13 | 7.24 |
| In plasma | | |
| ORP | 136 mV | 121 mV |
| Lactic acid | 16.8 mg/dL | 18.2 mg/dL |
| Pyruvic acid | 0.8 mg/dL | 0.9 mg/dL |
| pH | 7.39 | 7.44 |
| CPK | 29475 U/L | 15854 U/L |
| Myoglobin | 1700 ng/mL | 840 ng/mL |
| LDH | 1550 IU/L | 1177 IU/L |
| Aldolase | 169.2 IU/L | 96.2 IU/L |

Measurement 1 and Measurement 2 were performed before and after minus ion irradiation treatment of the patient, respectively.

Before the minus ion irradiation treatment (Measurement 1), the intracellular ORP is very high (248 mV), indicating significant oxidation in the cells. For this reason, the driving power of $Na^+/H^+$ channel is reduced to cause a reduction of pH (7.13). Generally, the lactic acid concentration in the cell is slightly higher than that in the blood. In the present case, however, the lactic acid concentration (10.6 mg/dL) in the cell is much lower than that in the blood (16.8 mg/dL). In the red blood cells, there is no TCA circuit, i.e. only a glycolysis system exists. Therefore, in the red blood cells, glucose is decomposed to produce pyruvic acid, which in turn is converted into lactic acid. Thus, the fact that the the lactic acid concentration in the cell is much lower than that in the blood indicates that the metabolism in the cells is low.

Namely, the low pH and high ORP in the cells indicate an increase of acidity and oxidation which causes reduction of metabolism. The CPK, myoglobin, LDH and aldolase values are thus high, indicative of bad conditions of the patient.

As a result of the minus ion treatment (Measurement 2), the acidity and oxidation in the cells are in normal values. The lactic acid concentration in the cell is slightly higher than that in the blood, though the value per se is greater than the normal value. Although the CPK, myoglobin, LDH and aldolase values are still higher than the normal values, they decrease as a result of the minus ion irradiation treatment, indicating that the condition of the patient is improved.

EXAMPLE 3

A blood cell test according to the present invention was carried out for a patient (male, 4 years old) to determine oxidation-reduction potential (ORP), lactic acid concentration, pyruvic acid concentration and pH in the red blood cells in the same manner as described in Example 2. Also measured were oxidation-reduction potential (ORP), lactic acid concentration, pyruvic acid concentration and pH in the plasma in the conventional manner. The results are summarized in Table 4.

TABLE 4

|  | Measurement 1 | Measurement 2 |
|---|---|---|
| In red blood cell |  |  |
| ORP | 229 mV | 250 mV |
| Lactic acid | 17.5 mg/dL | 23.8 mg/dL |
| Pyruvic acid | 0.61 mg/dL | 0.4 mg/dL |
| pH | 7.11 | 7.28 |
| In plasma |  |  |
| ORP | 132 mV | 121 mV |
| Lactic acid | 15.9 mg/dL | 18.2 mg/dL |
| Pyruvic acid | 0.5 mg/dL | 0.6 mg/dL |
| pH | 7.33 | 7.37 |
| Blood glucose level | 380 mg/dL | 309 mg/dL |

Measurement 1 and Measurement 2 were performed before and after minus ion irradiation treatment of the patient, respectively. Before the minus ion irradiation treatment (Measurement 1), the lactic acid concentration in the cell is 17.5 mg/dL which is slightly higher than that in the blood (15.9) and that of the normal range (8 to 16 mg/dL). Further, the intracellular ORP is not high (229 mV), indicating oxidation in the cells is not in a high level. However, the pH is very low (7.11), indicating that the glycolysis in the cells does not proceed. After the minus ion irradiation treatment, the lactic acid concentration is high (23.8 mg/dL) and ORP is high (250 mV), suggesting that the oxidation in the cells occurs and the metabolism will decrease. However, the pH is in a good range, indicating that the glycolysis in the cells proceeds satisfactory. In fact, the blood glucose level is improved.

From the data of concentrations of organic acids (pyruvic acid and lactic acid), ORP and pH in the red blood cells and in the plasma, possibility of onset and conditions of diseases may be diagnosed. As a disease gets worse, the blood data changes in the following order:

(1) First stage: values of concentrations of organic acids in the in the red blood cells and in the plasma do not fall in standard range, or the balance between the concentrations of organic acids in the red blood cells and those in the plasma is not normal;

(2) Second stage: values of ORP in the in the red blood cells and in the plasma do not fall in standard range, or the balance between the ORP in the red blood cells and that in the plasma is not normal;

(3) Third stage: pH values in the red blood cells and in the plasma do not fall in standard range, or the balance between the pH value in the red blood cells and that in the plasma is not normal.

Table 5 shows standard values.

TABLE 5

|  | Reference value |
|---|---|
| In red blood cell |  |
| ORP | 235 mV or less |
| Lactic acid | 8–16 mg/dL |
| Pyruvic acid | 0.5–1.2 mg/dL |
| pH | 7.24–7.30 |
| In plasma |  |
| ORP | 130 mV or less |
| Lactic acid | 6–14 mg/dL |
| Pyruvic acid | 0.3–0.9 mg/dL |
| pH | 7.36–7.42 |
| CPK | 35–200 U/L |
| Myoglobin | 60 ng/mL |
| LDH | 106–211 IU/L |
| Aldolase | 0–6 IU/L |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A blood test method comprising the steps of
    (a) centrifuging a mammalian blood sample into a plasma and blood cells;
    (b) removing buffy coats from said blood cells to obtain red blood cells containing solutes confined therewithin;
    (c) washing said red blood cells with a buffered physiological saline solution and isolating said washed blood cells;
    (d) mixing said washed red blood cells with a buffered physiological saline solution to obtain a suspended liquid;
    (e) centrifuging said suspended liquid to remove a supernatant and to obtain a red blood cell layer;
    (f) mixing said red blood cell layer with a hypertonic solution and maintaining the resulting suspension at a temperature of 25 to 40° C. for a period of time sufficient for the solutes confined in the red blood cells to penetrate into the hypertonic solution;
    (g) centrifuging the suspension to obtain a supernatant containing the solutes; and
    (h) measuring the supernatant for at least one factor selected from the group consisting of glucose concentration, pyruvic acid concentration, lactic acid concentration and oxidation-reduction potential.

2. A blood test method as claimed in claim 1, wherein step (a) comprises centrifuging the blood sample at a force of 130×g to 200×g for 5 to 10 minutes.

3. A blood test method as claimed in claim 1, wherein step (b) comprises mixing the blood cells with a sedimentation agent, and centrifuging the resulting mixture at a force of 800×g to 1,200×g for 7 to 12 minutes.

4. A blood test method as claimed in claim 1, wherein step (c) comprises mixing said red blood cells with a phosphate buffered physiological saline solution, and centrifuging the resulting mixture at a force of 130×g to 200×g for 5 to 10 minutes.

5. A blood test method as claimed in claim 1, wherein step (d) comprises mixing said washed red blood cells with a phosphate buffered physiological saline solution in an amount so that the suspended liquid has a hematcrit value of 40 to 50%.

6. A blood test method as claimed in claim 1, wherein step (e) comprises centrifuging the suspended liquid at a force of 130×g to 200×g for 5 to 10 minutes, and removing the supernatant.

7. A blood test method as claimed in claim 1, wherein step (f) comprises mixing the red blood layer with a 5 to 10% weight saline solution and maintaining the resulting mixture at a temperature of 35 to 38° C. for 7 to 15 minutes.

8. A blood test method as claimed in claim 1, wherein step (g) comprises centrifuging the suspension at a force of 1,500×g to 2,000×g for 7 to 12 minutes.

9. A blood test method as claimed in claim 1, wherein step (h) comprises measuring the supernatant for at least one factor selected from the group consisting of glucose concentration, pyruvic acid concentration and lactic acid concentration using an automatic biochemical analyzer.

10. A blood test method as claimed in claim 1, wherein step (h) comprises measuring the supernatant for an oxidation-reduction potential using a potentiometer.

11. A blood test method as claimed in claim 1, wherein said at least one factor includes glucose concentration.

12. A blood test method as claimed in claim 11, further comprising:

evaluating glucolysis in the red blood cells on the basis of results of said measuring.

13. A blood test method as claimed in claim 1, wherein, said at least one factor includes oxidation-reduction potential and further comprising:

measuring the oxidation-reduction potential of the plasma; and determining if the measured oxidation-reduction potential of the plasma and the measured oxidation-reduction potential of the supernatant fall within standard ranges.

14. A blood test method as claimed in claim 1, wherein said at least one factor includes lactic acid concentration and further comprising:

measuring lactic acid concentration in the plasma;

comparing lactic acid concentration in the supernatant with lactic acid concentration in the plasma; and evaluating metabolism of the red blood cells based on the results of the comparison.

15. A blood test method as claimed in claim 1, wherein said at least one factor includes pyruvic acid concentration.

16. A blood test method as claimed in claim 1, wherein said at least one factor includes pH.

* * * * *